United States Patent [19]

Yamamoto et al.

[11] Patent Number: 4,970,151
[45] Date of Patent: Nov. 13, 1990

[54] PLANT CULTURE CELL AND USE THEREOF

[75] Inventors: Yoshikazu Yamamoto, Neyagawa; Ryuzo Mizuguchi, Yawata; Toshiko Shibata, Ichikawa, all of Japan

[73] Assignee: Nippon Paint Co., Ltd., Osaka, Japan

[21] Appl. No.: 283,934

[22] Filed: Dec. 12, 1988

Related U.S. Application Data

[63] Continuation of Ser. No. 848,961, Apr. 7, 1986, abandoned.

[30] Foreign Application Priority Data

| Apr. 6, 1985 | [JP] | Japan | 60-73220 |
| Feb. 26, 1986 | [JP] | Japan | 61-42738 |
| Feb. 26, 1986 | [JP] | Japan | 61-42739 |
| Feb. 26, 1986 | [JP] | Japan | 61-42740 |

[51] Int. Cl.$^5$ .......................................... C12P 17/18
[52] U.S. Cl. .................... 435/119; 435/41; 435/240.46; 435/240.48
[58] Field of Search .......... 435/240.4, 240.45, 240.46, 435/240.47, 240.48, 240.49, 240.5, 240.51, 240.54, 41, 119; 424/59, 195.1, 94.1; 514/184; 549/435, 427

[56] References Cited

FOREIGN PATENT DOCUMENTS

| 0052001 | 5/1982 | European Pat. Off. . |
| 0196533 | 10/1986 | European Pat. Off. . |
| 0206691 | 12/1986 | European Pat. Off. . |

OTHER PUBLICATIONS

Ammirato, PV (1984) in "Cell Culture and Somatic Cell Genetics of Plants", IK Vasil, ed., Academic Press, NY, pp. 141-142.

Evans et al. (1981) in "Plant Tissue Culture, Methods and Applications in Agriculture", TA Thorpe, ed., Academic Press, NY, pp. 53-55.

Ima et al. (1987) Planta Med. 53(2): 228, Abstract cited.

Primary Examiner—Charles F. Warren
Assistant Examiner—Charles E. Cohen
Attorney, Agent, or Firm—Wenderoth, Lind and Ponack

[57] ABSTRACT

Disclosed is cultured plant cell derived from tissues or cells of a plant belonging to Hydrocotyle genus (waterpennyworts) and Centella genus, a culture method therefor, and a blood coagulation component and an therapeutic agent for mental disease obtained the cultured plant cells.

2 Claims, 1 Drawing Sheet

PLANT CULTURE CELL AND USE THEREOF

This application is a continuation of now abandoned application Ser. No. 848,961, filed April 7, 1986.

FIELD OF THE INVENTION

The present invention relates to a plant culture cell derived from tissues or cells of plants belonging to *Hydrocotyle genus* (water-pennywort) and *Centella genus*, a culture method therefor, and a blood coagulation component and an therapeutic agent for mental disease obtained therefrom.

BACKGROUND OF THE INVENTION

The number of blood examinations is increasing because a wealth of data relating to conditions of health and disease is obtained by examination and analysis of blood, particularly serum. Intensive studies have been made to achieve an effective separation of serum. It has been known that separation is effectively made by using a serum separating agent (a partition-forming polymer material having a specific gravity between serum and blood solids) together with a blood coagulation accelerating agent. As the blood coagulation accelerating agents, silicate particles, fibrous materials, calcium compound particles and the like are exemplified, but they do not exhibit sufficient blood-separation capacity They even exhibit hemolysis occasionally. Accordingly, blood coagulation accelerating agents having excellent properties are desired It is found that a water-pennywort ("New Picture Book of the Japanese Flora" to Makino, published by Hokuryukan, page 433), which has been used for stopping bleeding by people, has the blood coagulation property. Since the water-pennywort (*Hydrocotyle genus*) is a perennial herb growing naturally in a yard or field and has a height of less than 10 cm, it is difficult to obtain effective components in large quantities.

Components obtained from plants may be classified based on their functions to a blood coagulation component which indicates a blood coagulating function and a component for improving mental disease which improves mental diseases. One of the inventors of the present invention previously found that an important component in the blood coagulation component is l-sesamin represented by the following formula:

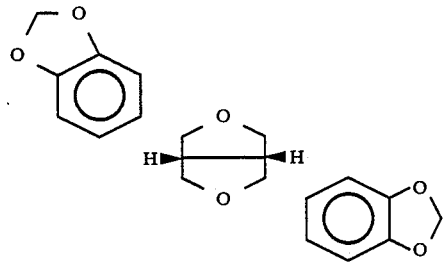

It is difficult to produce l-sesamine in large quantities even by way of chemical syntheses, because l-sesamine is an optically active substance having a complicated chemical structure.

The present invention enables the production of the blood coagulation component and a mental disease therapeutic component, particularly a component for suppressing neurotropic spasm, in large quantities by way of adopting a plant tissue culture technique.

The plant tissue culture method can grow plants in very high rates in comparison with natural plants growing in a year or month term. Accordingly, the object substance can be obtained in a short term. The plant tissue culture also is not affected by weather and the necessary components can be gathered without extensive labor. Also, it can be and it can be intentionally carried out as an industrial scale.

The culture cell or culture tissue of *Hydrocotyle genus* and *Centella genus*, however, has not been reported. It has been found that the components obtained from the culture cells or culture tissue of the plants mentioned above exhibit a blood coagulation property.

SUMMARY OF THE INVENTION

The present invention provide a plant culture cell derived from a tissue or cell of a plant belonging to *Hydrocotyle genus* or *Centella genus*.

The present invention also provides a method for culturing a plant culture cell comprising culturing a tissue or cell of a plant belonging to *Hydrocotyle genus* or *Centella genus* in or on a culture medium.

The present invention further provides a blood coagulation component obtained from the plant culture cell mentioned above.

The present invention additionally provides a mental disease therapeutic agent containing a mental disease therapeutic component derived from the plant culture cell mentioned above.

Detailed description of the present invention

Figure 1:
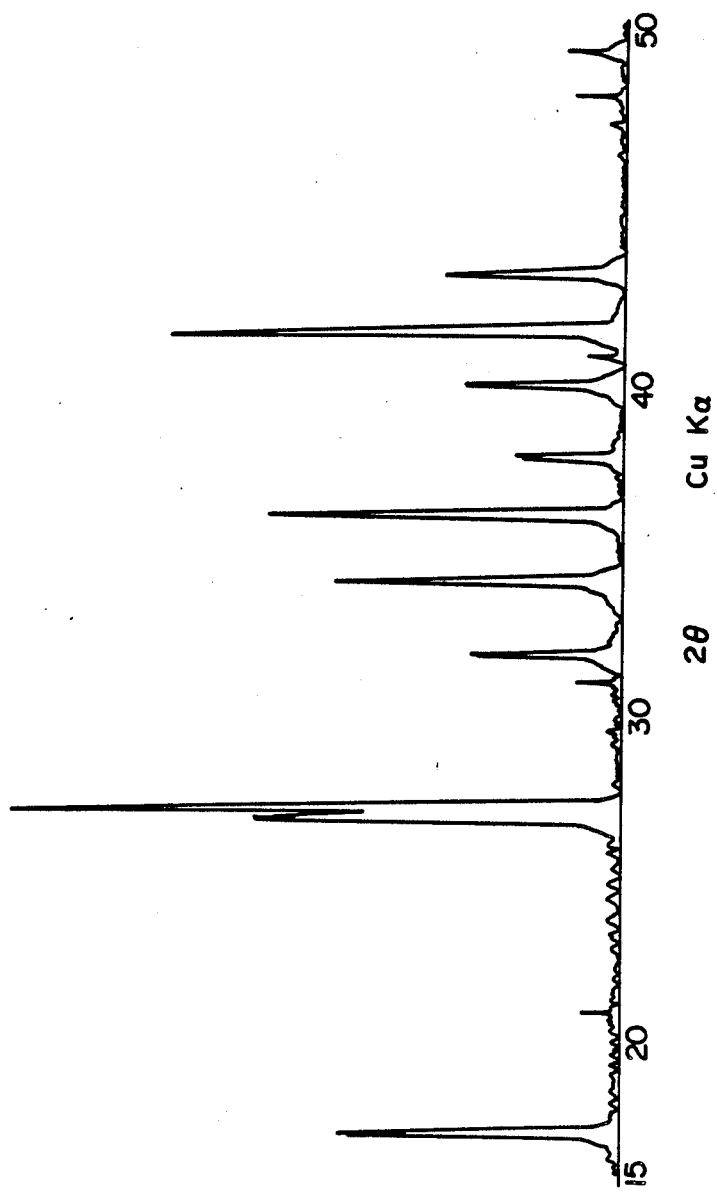

In the present invention, the plant employed belongs to *Hydrocotyle genus* or *Centella genus*. Examples of the plants are *Hydrocotyle sibthorpioides*, *H. Maritima*, *H. japonica*, *H. ramiflora*, *H. nepalensis*, *Centella asiatica* and the like.

The portion of the plant to be cultured is all tissues of the plant belonging to *Hydrocotyle genus* or *Centella genus*. A division tissue and a node tissue are preferred because of high propagation rate of the culture cell or culture tissue derived therefrom. By "division tissue" is meant a tissue contributing to growth of plants by way of cell division in the tissue of plants. Preferred are a terminal bud and a lateral bud. By "node tissue" is meant a portion of the stalk to which a leaf is attached or being attached, which is contrasted with a tissue between nodes.

The cultured plant cells are plant cells derived from the tissue or cell of plants and artificially cultured in a container. The cultured plant cells include callus tissues, differentiated cultured tissues, cultured organ tissues and the like. The callus tissues (hereinafter simply referred to "callus") are cultured plant cells lump only consisting of shapeless undifferentiated cells propagated over solid culture medium containing plant hormones or in liquid culture medium containing the plant hormones. The differentiated tissues are cultured plant cells lump composed of tissue having been differentiated (such as a root, a bud or a shoot), and undifferentiated cells. Included are adventive buds (consisting of bud tissues and undifferentiated cells), adventive roots (consisting of root tissues and undifferentiated cells) and cormus cultivated tissues (consisting of shoot tissues and undifferentiated cells). The cultured organs are cultured plant cells lump solely consisting of differentiated tissues which include cultures roots, cultures shoot and the like.

A method for culturing cells is illustrated by adopting *Hydrocotyle maritima* as an example, but it can apply to the other plants classified as *Hydrocotyle genus* and *Centella genus* as well.

A stalk containing petioles and terminal buds of *Hydrocotyle maritima* is washed with a deionized water and various germs on the surface of it are removed by immersing in a 70% ethanol for 5 to 10 minutes and then in a 10% bleaching powder solution for 5 to 10 minutes followed by removing a remaining sterilizing agent with a sterilized distilled water. The sterilized petiole may be cut with a sterilizing knife to a portion having a suitable size. The terminal bud can also be cut off from the sterilized stalk with the sterilized knife and a sterilized pincette. The cut portion is placed on an inorganic synthetic culture medium preferably containing an auxin and to culture it.

Besides the above petiole or terminal bud, the plant tissue or cell to be cultured may be any other portions, such as a division tissue or a node tissue including a lateral bud, a leaf, a stalk, or a root. The cell obtained by treating the above mentioned tissue or cell, such as a protoplast can also be employed. Further a tissue or cell which has already been cultured (hereinafter "culture tissue" or "culture cell") is used.

The culture medium for culturing the plant tissue is a known inorganic synthetic agar culture medium to which is added a trace organic material, a carbon source, a various natural and an extract together with an auxin and/or a cytokinin. Typical examples of the culture mediums are a White culture medium, a Linsmaier-skoog, a Murashige-skoog culture medium and the like. These culture medial can be changed in their composition.

The trace organic materials include vitamines such as thiamine hydrochloride, pyridoxine hydrochloride, nicotinic acid and the like, amino acids such as glycine, asparagine and the like and heptahydric alcohols such as inositol, sorbitol and the like. The culture medium without adding the trace organic materials may give rise to propagation in some cases.

The carbon sources include carbohydrates such as sucrose, glucose, maltose and the like, organic acids such as acetic acids and the like, alcohols such as methanol, glycerol and the like. Preferred are sucrose and glucose because of the rapid growing rate of plant cell. The concentration of the carbon sources is within the range of 1 to 10 %w/v, preferably 3 to 5 %w/v.

Examples of the auxins are 2,4-dichlorophenoxyacetic acid (2,4-D), beta-indoleacetic acid (IAA), alpha-naphthaleneacetic acid (NAA), a mixture thereof and the like. The amount of the auxins is not more than $10^{-4}$, preferably not more than $10^{-5}$, more preferably within the range of $10^{-7}$ to $10^{-5}$. The cytokinins includes kinetin, benzyladenine, and a mixture thereof and the like. The amount of the cytokinin is not more than $10^{-4}$, preferably not more than $10^{-5}$, more preferably within the range of $10^{-7}$ to $10^{-5}$.

Examples of the natural extracts mentioned above are casein hydrolysates (0.01 to 2 %w/v), coconuts milk (5 to 20 %w/v), yeast extracts (0.01 to 2 %w/v), malt extracts (0.01 to 2 %w/v), a mixture thereof and the like. Culture can be carried out by exposing to light, preferably light having more than 1,000 lx for more than 16 hours per day.

The resultant culture cells can be either a tissue culture callus or a differentiated tissue depending on the portion of the plant tissue being cultured or a combination of the auxins with the cytokinins. Callus is generally obtained in many conditions. In case where the tissue is a division tissue, especially a terminal bud or a lateral bud, where the auxins are indoleacetic acid or naphthaleneacetic acid, or where the culturing is conducted under light especially having 5,000 lx for more than 16 hours, a differentiated tissue, particularly a cormus culture tissue can be obtained.

The derivation for differentiating the callus to an adventive bud depends on the amount of the auxins and cytokinin or the conditions of light exposure. Preferred condition is set to a combination of 0 to $10^{-6}$ M of the auxin (for example 2,4-D) with 0 to $10^{-6}$ of the cytokinin (for example kinetin) and light exposure for more than 16 hours at 5,000 lx.

Adventive roots are formed from the callus depending on the amount of the auxins and cytokinins. Preferred amount is a combination of 0 to 10-6 M of the auxin, typically indole acetic acid or naphthaleneacetic acid and 0 to $10^{-6}$ M of the cytokinin.

The root cultures can be generally derived from the adventive root by cutting off the end portion containing growing point of the adventive root using a knife and placing it on the agar culture medium or into the liquid culture medium to culture. Besides the adventive roots, roots which are developed from a seed under a sterilized condition or which is artificially developed from a plant by inoculating Agrobacterium lisogenase can be employed. As the culture medium, it is preferred that the auxin, preferably indole acetic acid or naphthaleneacetic acid, is added in an amount of 0 to $10^{-6}$ and the cytokinin is added in an amount of 0 to $10^{-6}$. The culture is conducted either in a dark place at 20 to 30 °C. for solid culturing medium or in a shaker at 50 to 150 rpm for liquid culture medium, but these are not limited.

A cultured shoot can be generally derived from the shoot culture tissues mentioned above as generally described relating to the cultured roots.

The cultured cells can be industrially obtained by culturing and propagating in a generally similar method of culturing microbes. The liquid culture can be classified into a shaking culture method in a shaker and a bubbling culture method by introducing sterilized air into a container made of glass, metal and the like.

The blood coagulation component of the present invention can be obtained from the culture cell mentioned above by a known separating method, such as extraction or heating. A blood coagulation component obtained by extraction is preferred because of high blood coagulation property. The extraction method is illustrated by employing the culture cells of *Hydrocotyle maritima* as an example.

The culture cell obtained above is dried by freeze drying or air drying at 60° C. for 24 hours or at 110° C. for 3 hours to remove water. The dried cultured cells are extracted in acetone by a Soxhlet apparatus, a digestion method, or a maceration method. Instead of acetone, the other organic solvent such as methanol, ethanol and the like may be used for the extraction. Acetone is removed from the extract to obtain a concentrated acetone extract having blood coagulation property and hemostasis property. The blood coagulation component contains l-sesamine. l-Sesamine can be obtained from the resultant acetone extract. For obtaining l-sesamine, water and ethyl acetate are added to the concentrated acetone extract to distribute into a water layer and an organic layer. Instead of ethyl acetate, other organic solvents such as chloroform, methylene dichloride, n-hexane, ethyl ether, benzene, methyl acetate, n-pentane, cyclohexane, petroleum ether can be employed. The distributed organic layer is subjected to a distillation to concentrate. The concentrated extract is subjected to a separation by column chromatography to obtain a crude 1-sesamine. Besides column chromatography, other separation methods, such as a thin-film chromatography can be employed.

The resultant 1-sesamine may be identified by silica gel G film chromatography, infrared spectrum and NMR spectrum.

The blood coagulation component can be used for the purpose of separation of serum from blood in a short time for a serum examination, for the purpose of shortening the determination time for a blood coagulation examination, for the purpose of stopping bleeding from a living body, and the like.

The blood coagulation component of the present invention may be applied to the material to be examined, such as blood, in the form of power or an aqueous suspension, or it may be coated on the wall of a container for serum separation in the form of a solution or a dispersion. It may further be coated on beads, such as glass beads in the form of a solution or a dispersion and placed in test tubes. The amount to be used for blood coagulation is not limited, but 0.01 to 500 mg of the extract per 1 ml of blood is sufficient for blood coagulation. Especially, the container for serum separation, which has been coated with the blood coagulation component of the present invention, can precipitate the blood more rapidly in comparison with a conventional one. Accordingly, the container is of value for rapid blood examination.

The blood coagulation component can be used with a known blood coagulation accelerating agent, for example, fine powder such as silica, caoline, glass and the like and fibrous material to enhance the coagulation property.

It has been also found that the plant extract or the plant culture tissue of the present invention, per se, has mental disease therapeutic function. In addition, an extract from plants also has the same function. The extraction can be conducted as in the case of the extraction of the blood coagulation component. The obtained mental disease therapeutic component can be used as it is or in the form of a dried powder. The mental disease therapeutic component may be combined with conventional additives. The formulation form of the disease improving agent is limited, including powder, tablet, liquid and the like.

The dosage of the mental disease therapeutic agent is not limited and can vary depending on the purpose or upon disease conditions. For example, in case of the acetone extract mentioned above, the dosage is 1 to 1,000 mg/day /weight.

The mental disease therapeutic agent of the present invention improves many mental diseases, such as mental uneasiness, melancholia, nicotine toxicosis, alcoholism, morphinomenia, antihypotic toxicosis and the like.

The present invention is illustrated by the following examples, but they are not construed as limiting the present invention.

EXAMPLE 1

A 3cm stalk of *Hydrocotyle maritima* containing terminal buds was washed with water and immersed in a 70% ethanol for 5 minutes and then in a 10% bleaching powder for 10 minutes to sterilize. The stalk was further immersed in a sterilized distilled water several times to remove remaining sterilizing agent. The sterilized stalk was cut to a fragment containing a terminal bud having a length of 5 to 1mm with a sterilized knife and a sterilized pincette under a stereomicroscope. The obtained sterilized fragment of *Hydrocotyle maritima* was placed on a synthetic agar plate having the following described composition. The culture medium was made by adding 3% w/v of sucrose, $10^{-6}$ M of alphanaphthaleneacetic acid, 0.1 ppm of thiamine hydrochloride, 0.5 ppm of pyridoxine hydorochloride, 0.5 ppm of nicotinic acid, 2 ppm of glycine and 100 ppm of inositol to an inorganic salt culture medium of Murashige-skoog to adjust to pH 6.0, adding 0.8 %w/v of agar and sterilizing in a conventional manner.

The fragment placed on the culture medium was cultured at a culture temperature of 25° C. under light of 5,000 lx. After three weeks, shoot cultured tissues were developed from the fragment. The shoot cultured tissues were divided to two portions after one month and transferred to other culture mediums having the same composition to continue culturing at 25° C. The same treatment was repeated every 2 weeks to obtain stable shoot cultured tissues.

REFERENCE EXAMINATION 1

The shoot cultured tissues of *Hydrocotyle maritima* propagated in Example 1 was taken from the solid culture medium and dried at 60° C. for 24 hours to obtain 10g of dried tissues. The dried tissues were ground in a mortar and the chemical compound extracted by acetone using a Soxhlet extractor for 8 hours for three times. The acetone extract was concentrated to about 50ml and then charged in a separating funnel, to which 50ml of water and 100ml of ethyl acetate were added and shaken to divide the ethyl acetate layer. The same operation was repeated several times and the obtained ethyl acetate solution was concentrated and subjected to a distillation to obtain an ethyl acetate extract. The extract was dispensed by a silica gel column chromatography to obtain 15mg of 1-sesamine.

The resultant product was subjected to an infrared spectrum and a NMR spectrum and found to be identical to the spectrum of an identified 1-sesamine. The spot and developed color by a silica 1 G thin film chromatography using a 9/1 mixture of chloroform/ethyl acetate or a 7/3 mixture of n-hexane/ethyl acetate was identical to those of the 1-sesamine which has been identified. The product was identified as 1-sesamine.

EXAMPLE 2

Shoot cultured tissues of *Hydrocotyle sibthorpioides* were formed by treating as generally described in Example 1 with the exception that *Hydrocotyle sibthorpioides* was employed instead of *Hydrocotyle maritima*. 1-Sesamine was obtained from the shoot cultured tissues.

EXAMPLE 3

Shoot cultured tissues of *Hydrocotyle nepalensis* were formed by culturing as generally described in Example 1 with the exception that *Hydrocotyle nepalensis* was employed instead of *Hydrocotyle maritima*. 1-Sesamine was also obtained from the shoot cultured tissues.

EXAMPLE 4

Shoot cultured tissues of *Hydrocotyle japonica* were obtained by culturing as generally described in Example 1 with the exception that *Hydrocotyle japonica* was employed instead of *Hydrocotyle maritima*. 1-Sesamine was also obtained from the cormus culture tissue.

EXAMPLE 5

Shoot cultured tissues of *Hydrocotyle ramiflora* were formed by culturing as generally described in Example 1 with the exception that *Hydrocotyle ramiflora* was employed instead of *Hydrocotyle maritima*. 1-Sesamine was also obtained from the cormus culture tissue.

EXAMPLE 6

Shoot cultured tissues of *Centella asiatica* were formed by culturing as generally described in Example 1 with the exception that *Centella asiatica* was employed instead of *Hydrocotyle maritima*. 1-Sesamine was also obtained from the cormus culture tissue.

EXAMPLE 7

A stalk of *Hydrocotyle maritima* containing node tissues was washed with water and immersed in a 70% ethanol for 5 minutes and then in a 10% bleaching powder for 10 minutes to sterilize. The stalk was further immersed in a sterilized distilled water several times to remove remaining sterilizing agent. The sterilized stalk was cut to a fragment containing a node tissue having a length of 0.5 to 1mm with a sterilized knife. The obtained sterilized fragment of *Hydrocotyle maritima* was placed on a synthetic agar plate having the following described composition. The culture medium was made by adding 3% w/v of sucrose, $10^{-5}$ M of kinetin, $10^{-6}$ of 2,4 dichlorophenoxyacetic acid, 0.1ppm of thiamine hydrochloride, 0.5ppm of pyridoxine hydorochloride, 0.5ppm of nicotinic acid, 2ppm of glycine and 100ppm of inositol to an inorganic salt culture medium of Murashigeskoog to adjust to pH6.0, adding 0.8%w/v of agar and sterilizing in a conventional manner.

The fragment placed on the culture medium was cultured at the culture temperature of 25° C. After about one week, a light yellow callus was developed from near the cut portion. The grown-up callus was divided to two portions after one month and transferred to other culture mediums having the same composition to continue culturing at 25° C. The same treatment was repeated every 2 or 3 weeks to obtain a stable callus.

The propagation ratio of the callus in two weeks is shown in Table 1 infra.

The callus of *Hydrocotyle maritima* was taken from the solid culture medium and dried at 60° C. for 24 hours to obtain a dried callus. The dried calluses were ground in a mortar and extracted by acetone using a Soxhlet extractor for 8 hours for three times. The acetone was removed by distillation to obtain 1.5g of an acetone extract. The extract had blood coagulation function.

Bananas containing 5ml of a triolein in which 200mg of the extract was dissolved were fed to a monkey (2.1Kg) having alcoholism symptoms for seven days. The alcoholism symptoms, such as shaking and stiffening of muscle, were improved.

EXAMPLE 8

A callus of *Centella asiatica* was formed by culturing as generally described in Example 1 with the exception that *Centella asiatica* was employed instead of . *Hydrocotyle maritima*.

The propagation ratio of the callus in two weeks is shown in Table 1 infra.

The acetone extract of the callus showed blood coagulation function and improving symptoms of alcoholism.

EXAMPLE 9

A callus derived from internode tissue of *Hydrocotyle maritima* was formed by culturing as generally described in Example 1 with the exception that the internode tissue was employed instead of the node tissue.

The propagation ratio of the callus in two weeks is shown in Table 1 infra.

EXAMPLE 10

A callus derived from an internode tissue of *Centella asiatica* was formed by culturing as generally described in Example 8 with the exception that the internode tissue was employed instead of the node tissue.

The propagation ratio of the callus in two weeks is shown in Table 1 infra.

TABLE 1

| Example | Propagation ratio in two weeks |
|---------|-------------------------------|
| 7 | 6.8 |
| 8 | 6.4 |
| 9 | 3.1 |
| 10 | 2.5 |

EXAMPLE 11

A petiole of *Hydrocotyle maritima* was washed with water and immersed in a 70% ethanol for 5 minutes and then in a 10% bleaching powder for 10 minutes to sterilize. The petiole was further immersed in a sterilized distilled water several times to remove remaining sterilizing agent. The sterilized petiole was cut to a fragment having a length of 0.5 to 1mm with a sterilized knife. The obtained sterilized fragment of *Hydrocotyle maritima* was placed on a synthetic agar plate having the following described composition. The culture medium was made by adding 3% w/v of sucrose, $10^{-5}$ of kinetin, $10^{-6}$ M of 2,4-dichlorophenoxyacetic acid, 0.1ppm of thiamine hydrochloride, 0.5ppm of pyridoxine hydorochloride, 0.5ppm of nicotinic acid, 2ppm of glycine and 100ppm of inositol to an inorganic salt culture medium of Murashigeskoog to adjust to pH6.0, adding 0.8%w/v of agar and sterilizing in a conventional manner.

The fragment placed on the culture medium was cultured at a culture temperature of 25° C. After one week, a light yellow callus was developed from the fragment. The grown-up callus was divided into several portions after one month and transferred to other culture mediums having the same composition to continue culturing at 25° C. The same treatment was repeated every 4 to 6 weeks to obtain a stable callus.

The callus of *Hydrocotyle maritima* was taken from the solid culture medium and dried at 60° C. for 24 hours to obtain dried tissues of 30g. The dried tissues were ground by a mortar and extracted by acetone using a Soxhlet extractor for 8 hours for three times. The acetone solution was concentrated to about 50ml and then charged in a separating funnel, to which 50ml of water and 100ml of ethyl acetate were added and shaken to collect the ethyl acetate layer. The same operation was repeated several times and the obtained ethyl acetate solution was concentrated and subjected to a distillation to obtain an ethyl acetate extract. The extract was dispensed by a silica gel column chromatography to obtain 12mg of 1-sesamine (0.04 % based on dried weight).

The resultant product was subjected to an infrared spectrum and a NMR spectrum and found to be was identical to the spectrum of the identified 1-sesamine. The spot and developed color by a silica gel G thin film chromatography using a 9/1 mixture of chloroform-/ethyl acetate or a 7/3 mixture of n-hexane/ethyl acetate was identical to those of the identified as 1-sesamine. THe product was identified 1-sesamine.

EXAMPLE 12

The callus of *Hydrocotyle maritima* obtained in Example 11 was transferred onto a synthetic agar culture medium having the following described composition. The culture medium was made by adding 3% w/v of sucrose, $10^{-7}$ of kinetin, $10^{-7}$ M of alpha-naphthaleneacetic acid, 0.1ppm of thiamine hydrochloride, 0.5ppm of pyridoxine hydorochloride, 0.5ppm of nicotinic acid, 2ppm of glycine and 100ppm of inositol to an inorganic salt culture medium of Murashige-skoog to adjust to pH6.0, adding 0.8%w/v of agar and sterilizing in a conventional manner. The culturing was conducted to differentiate an adventive bud after one week.

The obtained adventive bud was treated as generally described in Example 11 to obtain crude 1-sesamine of 8mg (0.05% based on dried culture material weight).

EXAMPLE 13 to 17

Adventive roots were obtained by treating as generally described in Example 12 with the exception that *Hydrocotyle sibthorpioides, H. nepalensis, H. ramiflora, H. japonica* or *Centella asiatica* were respectively employed instead of *Hydrocotyle maritima*.

EXAMPLE 18

The callus from *H. maritima* obtained in Example 11 was cultured in a dark place at 25 ° C., 120 rpm in liquid culture medium with the exception that $10^{-6}$ M of indole acetic acid was employed instead of kinetin and alphanaphthaleneacetic acid to obtain adventive root after two weeks.

EXAMPLE 19 to 23

Adventive roots were obtained by treating as generally described in Example 18 with the exception that *Hydrocotyle sibthorpioides, H. nepalensis, H. ramiflora, H. japonica* or *Centella asiatica* were respectively employed instead of *Hydrocotyle maritima*.

EXAMPLE 24

The end portion of the adventive root obtained in Example 18 was cut off and cultured as generally described in Example 18 to obtain culture roots having prolonging or dividing propagation ability.

EXAMPLE 25 to 29

Adventive roots were obtained by treating as generally described in Example 24 with the exception that *Hydrocotyle sibthorpioides, H. nepalensis, H. ramiflora, H. japonica* or *Centella asiatica* were respectively employed instead of *Hydrocotyle maritima*.

Example 30

The end portion composed of the shoot of the stalk and bud cultured tissues obtained in Example 1 was cut off and transferred to the liquid culture medium similar to Example 1. Culturing was continuously conducted at 120 rpm, 25 ° C. under light of 5,000 lx to obtain cultured shoot having propagating ability of prolonging and branching.

EXAMPLE 31 to 35

Cultured shoots were obtained by treating as generally described in Example 30 with the exception that the cormus culture tissue of *Hydrocotyle sibthorpioides, H. nepalensis, H. ramiflora. H. japonica* or *Centella asiatica* were respectively employed instead of the cormus culture tissue of *Hydrocotyle maritima*.

EXAMPLE 36

Callus tissues of *H. maritima* were obtained as treated generally as described in Example 11 to extract 1-sesamine with the exception that *H. sibthorpioides* was employed instead of *H. maritima*.

EXAMPLE 37

Callus tissues of *Hydrocotyle nepalensis* were formed by culturing as generally described in Example 11 with the exception that *Hydrocotyle nepalensis* was employed instead of *Hydrocotyle maritima*. 1-Sesamine was also obtained from the tissue culture callus.

EXAMPLE 38

Callus tissues of *H. japonica* were formed by culturing as generally described in Example 11 with the exception that *H. japonica* was employed instead of *H. maritima*. 1-Sesamine was also obtained from the tissue culture callus.

EXAMPLE 39

Callus tissues of *H. ramiflora* were formed by culturing as generally described in Example 11 with the exception that *H. ramiflora* was employed instead of *H. maritima*. 1-Sesamine was also obtained from the tissue culture callus.

EXAMPLE 40

Callus tissues of *Centella asiatica* were formed by culturing as generally described in Example 11 with the exception that *C. asiatica* was employed instead of *Hydrocotyle maritima*. 1-Sesamine was also obtained from the callus tissues.

EXAMPLE 41

A petiole of *Hydrocotyle maritima* was washed with water and immersed in a 70% ethanol for 5 minutes and then in a 10% bleaching powder for 10 minutes to sterilize. The petiole was further immersed in a sterilized distilled water several times to remove remaining sterilizing agent. The sterilized petiole was cut to a fragment having a length of 0.5 to 1mm with a sterilized knife. The obtained sterilized fragment of *Hydrocotyle maritima* was placed on a synthetic agar plate medium having the following described composition. The culture medium was made by adding 3% w/v of cane sugar, $10^{-5}$ of kinetin, $10^{-6}$ M of 2,4-dichlorophenoxyacetic acid. 0.1ppm of thiamine hydrochloride, 0.5ppm of pyridoxine hydorochloride, 0.5ppm of nicotinic acid, 2ppm of glycine and 100ppm of inositol to an inorganic salt culture medium of Murashige-skoog to adjust to pH6.0, adding 0.8%w/v of agar and sterilizing in a conventional manner.

The fragment placed on the culture medium was cultured at a culture temperature of 25° C. After one week, a light yellow callus was developed from the fragment. The grown-up callus was divided into several portions after one month and transferred to other culture mediums having the same composition to continue culturing at 25° C. The same treatment was repeated every 4 to 6 weeks to obtain a stable callus.

The calluses of H. maritima were taken from the solid culture medium and dried at 60° C. for 24 hours to obtain 10g of dried calluses. The dried calluses were ground in a mortar and extracted by acetone using a Soxhlet extractor for 8 hours for three times. The obtained extract was subjected to a distillation for removing acetone to obtain a concentrated acetone extract of 1.5g.

EXAMPLE 42

One hundred mg of concentrated extract of Example 41 was dissolved in 10ml of acetone to form a solution. The solution was coated inside of a glass container (a) and a plastic container (b) for blood examination (inside diameter 13 mm and content volume 10 ml) containing serum separation gel to a height of about 30 to 35mm from the uppermost portion of the serum separation gel. The coated amount of the active material was within the range of 5 to 7mg. Blood coagulation time was determined by pouring 6ml of fresh human blood into the containers mentioned above to leave it at a constant room temperature and measuring the time required for flowability of the blood to disappear when the containers were tipped to the angle of 90°. The blood was subjected to a centrifuging at 1,500G for 5 minutes followed by dispensing the separated serum on the gel separated layer by tipping and measuring the amount. Also the degree of hemolysis was observed. The results are shown in Table 2.

COMPARATIVE EXAMPLE 1

Similar containers (a) and (b) containing serum separation gel was prepared without coating the blood coagulation component of the present invention. The tests were conducted as generally described in Example 42. The result are shown in Table 2.

TABLE 2

|  |  | Blood coagulation time (min) | Volume of dispersed serum (ml) | Hemolysis |
| --- | --- | --- | --- | --- |
| Ex. 42 | Container a | 21 | 3.0 | —[2] |
|  | Container b | 25 | 2.7 | — |
| Compartive | Container a | 35 | 3.0 | — |
| Ex. 1 | Container b | 80 | 0.9[1] | ±[3] |

[1]Fibrin is mixed in serum.
[2]No hemolysis is observed.
[3]A very little hemolysis is observed.

EXAMPLE 43

With the serum separated using the concentrated extract of Example 41, biochemical and immunochemical examinations were carried out. No bad effects were found.

EXAMPLE 44

A concentrated extract of Centella asiatica of 1.3g was obtained as generally treated in Example 41 with the exception that C. asiatica was employed instead of H. maritima.

EXAMPLE 45

The measurements were carried out as generally described in Example 42 with the exception that the concentrated extract of Example 44 was employed instead of that of Example 41. The results are shown in Table 3

TABLE 3

|  |  | Blood coagulation time (min) | Volume of dispersed serum (ml) | Hemolysis |
| --- | --- | --- | --- | --- |
| Ex. 45 | Container a | 19 | 2.0 | —[4] |
|  | Container b | 23 | 2.7 | — |

[4]No hemolysis is observed.

EXAMPLE 46

1-Sesamine (12mg) was obtained as generally described in Example 11 with the exception that a sterilized fragment of H. maritima was employed instead of the petiole of Example 11.

EXAMPLE 47

A crude 1-sesamine (8) mg was obtained from the callus of H. maritima in Example 46 as generally described in Example 12.

Example 48

Callus tissues of H. maritima were obtained as treated as generally described in Example 46 to extract 1-sesamine with the exception that H. sibthorpioides was employed instead of H. maritima.

EXAMPLE 49

Callus tissues of Hydrocotyle nepalensis were formed by culturing as generally described in Example 46 with the exception that Hydrocotyle nepalensis was employed instead of Hydrocotyle maritima. 1-Sesamine was also obtained from the callus tissues.

EXAMPLE 50

Callus tissues of H. japonica were formed by culturing as generally described in Example 46 with the exception that H. japonica was employed instead of H. maritima. 1-Sesamine was also obtained from the callus tissues.

EXAMPLE 51

Callus tissues of H. ramiflora were formed by culturing as generally described in Example 46 with the exception that H. ramiflora was employed instead of H. maritima. 1-Sesamine was also obtained from the callus tissues.

EXAMPLE 52

Callus tissues of Centella asiatica were formed by culturing as generally described in Example 46 with the exception that C. asiatica was employed instead of Hydrocotyle maritima. 1-Sesamine was also obtained from the callus tissues.

EXAMPLE 53 to 57

1-Sesamine was obtained by treating as generally described in Example 47 with the exception that *Hydrocotyle sibthorpioides, H. nepalensis, H. ramiflora, H. japonica* or *Centella asiatica* was respectively employed instead of *Hydrocotyle maritima*.

EXAMPLE 58 to 63

Adventive buds were obtained by treating as generally described in Example 41 with the exception that *Hydrocotyle sibthorpioides, H. nepalensis, H. ramiflora, H. japonica* or *Centella asiatica* were respectively employed instead of *Hydrocotyle maritima* of Example 47. A concentrated extract was obtained as generally described in Example 41.

EXAMPLE 64 to 69

Acetone concentrated extracts were obtained from the shoot cultured tissues of Example 1 to 6.

EXAMPLE 70 to 74

Acetone concentrated extracts were obtained by treating as generally described in Example 41 with the exception that *Hydrocotyle sibthorpioides, H. nepalensis, H. ramiflora, H. japonica* or *Centella asiatica* were respectively employed instead of *Hydrocotyle maritima*.

The same tests were conducted on the concentrated extracts of Example 58 to 63, 64 to 74. The result were similar to Example 42.

EXAMPLE 75

Four hundred grams of the calluses obtained from Example 41 was dispersed in a liquid culture medium of 10 liters in a jar of 14 liters and cultured for ten days at agitating rate of 50rpm, air supply rate of 5 1/min and temperature of 25 ° C. The culture medium employed was the same as that of Example 46. After ten days, about 4 kg of calluses was formed. Acetone concentrated extract of 20 g was obtained as generally described in Example 41.

EXAMPLE 75

The callus of *Hydrocotyle maritima* obtained in Example 41 was transferred onto a agar-plate having the following described composition. The culture medium was formed by adding 3% w/v of sucrose, $10^{-6}$ of indole acetic acid, 0.1ppm of thiamine hydrochloride, 0.5ppm of pyridoxine hydrochloride, 0.5ppm of nicotinic acid, 2ppm of glycine and 100ppm of inositol to an inorganic salt culture medium of Murashige-skoog to adjust to pH6.0, adding 0.8%w/v of agar and sterilizing in a conventional manner. The culturing was conducted at 25 ° C. and 120 rpm to form an adventive root after two weeks.

Acetone extract was obtained from the differentiated adventive root by treating as generally described in Example 41.

EXAMPLE 76 to 80

Acetone extract was obtained by treating as generally described in Example 75 with the exception that *Hydrocotyle sibthorpioides, H. nepalensis, H. ramiflora, H. japonica* or *Centella asiatica* were respectively employed instead of *Hydrocotyle maritima*.

EXAMPLE 81

The end portion of the adventive roots obtained by the process of Example 75 was cut off under sterile conditions and transferred to the same culture medium as Example 75 to form cultured roots having propagating ability of prolonging and dividing.

Acetone extract was obtained from the cultured roots by treating as generally described in Example 41.

Example 82 to 86

Acetone extract was obtained by treating as generally described in Example 81 with the exception that *Hydrocotyle sibthorpioides, H. nepalensis, H. ramiflora, H. japonica* or *Centella asiatica* was respectively employed instead of *Hydrocotyle maritima*.

Example 87

A 3cm stalk of Hydrocotyle maritima containing terminal buds was washed with water and immersed in a 70% ethanol for 5 minutes and then in a 10 % bleaching powder for 10 minutes to sterilize. The stalk was further immersed in a sterilized distilled water several times to remove remaining sterilizing agent. The sterilized stalk was cut to a fragment containing a terminal bud having a length of 5 to 1mm with a sterilized knife and a sterilized pincette under a stereomicroscope The obtained sterilized fragment of *Hydrocotyle maritima* was placed on a synthetic agar plate having the following described composition. The culture medium was made by adding 3 % w/v of sucrose, $10^{-6}$ M of alphanaphthaleneacetic acid, 0.1ppm of thiamine hydrochloride, 0.5ppm of pyridoxine hydrochloride, 0.5ppm of nicotinic acid, 2ppm of glycine and 100ppm of inositol to an inorganic salt culture medium of Murashige-skoog to adjust to pH6 0, adding 0.8%w/v of agar and sterilizing in a conventional manner.

The fragment placed on the culture medium was cultured at a culture temperature of 25° C. under light of 5,000 lx. After three weeks, shoot cultured tissues were developed from the fragment. The grown-up shoot cultured tissues were divided to two portions after one month and transferred to other culture mediums having the same composition to continue culturing at 25° C. The same treatment was repeated every 2 weeks to obtain stable shoot cultured tissues.

The end portion of the shoot was cut off under sterile conditions and transferred to the liquid culture medium having the same composition mentioned above Culturing was conducted at 120 rpm and 25 ° C. under light of 5,000 1× to obtain cultured shoot having propagating ability of prolonging and branching.

Acetone extract was obtained from cultured shoot as generally described in Example 41.

Example 92

Acetone extract was obtained by treating as generally described in Example 87 with the exception that *Hydrocotyle sibthorpioides, H. nepalensis. H. ramiflora, H. japonica* or *Centella asiatica* were respectively employed instead of *Hydrocotyle maritima*

EXAMPLE 93

1-Sesamine was obtained by treating as generally described in Example 46 using adventive roots as obtained in Example 76.

EXAMPLE 94 to 98

1-Sesamine was obtained by treating as generally described in Example 93 with the exception that *Hydrocotyle sibthorpioides, H. nepalensis, H. ramiflora, H.*

*japonica* or *Centella asiatica* were respectively employed instead of *Hydrocotyle maritima*.

Example 99

1-Sesamine was obtained by treating as generally described in Example 46 using adventive roots as obtained in Example 81.

EXAMPLE 100 to 104

1-Sesamine was obtained by treating as generally described in Example 99 with the exception that *Hydrocotyle sibthorpioides, H. nepalensis, H. ramiflora, H. japonica* or *Centella asiatica* were respectively employed instead of *Hydrocotyle maritima*.

EXAMPLE 105

1-Sesamine was obtained by treating as generally described in Example 46 using adventive roots as obtained in Example 87.

Example 106 to 110

1-Sesamine was obtained by treating as generally described in Example 105 with the exception that *Hydrocotyle sibthorpioides, H. nepalensis, H. ramiflora, H. japonica* or *Centella asiatica* were respectively employed instead of *Hydrocotyle maritima*.

EXAMPLE 111

Similar results were obtained by treating as generally described in Example 42 using adventive roots as obtained in Example 76.

EXAMPLE 112 to 116

Similar results were obtained by treating as generally described in Example 111 with the exception that *Hydrocotyle sibthorpioides, H. nepalensis, H. ramiflora, H. japonica* or *Centella asiatica* were respectively employed instead of *Hydrocotyle maritima*.

Example 117

Similar results were obtained by treating as generally described in Example 42 using adventive roots as obtained in Example 81.

Example 118 to 122

Similar results were obtained by treating as generally described in Example 117 with the exception that *Hydrocotyle sibthorpioides, H. nepalensis, H. ramiflora, H. japonica* or *Centella asiatica* were respectively employed instead of *Hydrocotyle maritima*.

Example 123

Similar results were obtained by treating as generally described in Example 42 using adventive roots as obtained in Example 87.

EXAMPLE 124 to 128

Similar results were obtained by treating as generally described in Example 123 with the exception that *Hydrocotyle sibthorpioides, H. nepalensis, H. ramiflora, H. japonica* or *Centella asiatica* were respectively employed instead of *Hydrocotyle maritima*.

Example 129

Bananas containing 5ml of a triolein in which 200mg of the acetone extract obtained in Example 41 was dissolved were fed to a monkey (2 Kg) having alcoholism symptoms for seven days. The alcoholism symptoms, such as shaking and stiffening of muscle, were improved.

EXAMPLE 130

One hundred gram of whole plant of *H. maritima* was dried for 24 hours at 60° C. to obtain 5.5 g of a dried plant. The dried plant was ground in a mortar and extracted by acetone using a Soxhlet extractor for 8 hours for three times. Acetone was distilled out from the acetone extract to obtain an acetone concentrated extract (1.1 g).

The test was conducted as described in Example 129 using the obtained acetone concentrated extract. The result showed similar improving effect of alcoholism symptoms.

Example 131

Acetone concentrated extract (1.4 g) was obtained by treating as generally described in Example 41 with the exception that the callus of *H. maritima* was employed as a plant tissue. The dried calluses were 10 g.

The test was conducted as described in Example 129 using the obtained acetone concentrated extract. The result showed similar improving effect of alcoholism symptoms.

Example 132

Acetone concentrated extract (1.0 g) was obtained by treating as generally described in Example 130 with the exception that whole plant of *H. maritima* was employed as a plant tissue. The dried calluses were 60 g.

The test was conducted as described in Example 129 using the obtained acetone concentrated extract. The result showed similar improving effect of alcoholism symptoms.

Example 133

Acetone concentrated extract (1.5 g) was obtained by treating as generally described in Example 41 with the exception that the callus of *H. japonica* was employed as a plant tissue. The dried calluses were 10 g.

The test was conducted as described in Example 129 using the obtained acetone concentrated extract. The result showed similar improving effect of alcoholism symptoms.

EXAMPLE 134

Acetone concentrated extract (0.8 g) was obtained by treating as generally described in Example 130 with the exception that whole plant of *H. japonica* was employed as a plant tissue. The dried calluses were 5.1 g.

The test was conducted as described in Example 129 using the obtained acetone concentrated extract. The result showed similar improving effect of alcoholism symptoms.

EXAMPLE 135

Acetone concentrated extract (1.3 g) was obtained by treating as generally described in Example 41 with the exception that the callus of *H. ramiflora* was employed as a plant tissue. The dried calluses were 10 g.

The test was conducted as described in Example 129 using the obtained acetone concentrated extract. The result showed similar improving effect of alcoholism symptoms.

Example 136

Acetone concentrated extract (0.9 g) was obtained by treating as generally described in Example 130 with the exception that whole plant of *H. ramiflora* was employed as a plant tissue. The dried calluses were 6.2 g.

The test was conducted as described in Example 129 using the obtained acetone concentrated extract. The result showed similar improving effect of alcoholism symptoms.

Example 137

Acetone concentrated extract (1.5 g) was obtained by treating as generally described in Example 41 with the exception that the callus of *H. nepalensis* was employed as a plant tissue. The dried calluses were 10 g.

The test was conducted as described in Example 129 using the obtained acetone concentrated extract. The result showed similar improving effect of alcoholism symptoms.

EXAMPLE 138

Acetone concentrated extract (0.8 g) was obtained by treating as generally described in Example 130 with the exception that whole plant of *H. nepalensis* was employed as a plant tissue. The dried calluses were 5.2 g.

The test was conducted as described in Example 129 using the obtained acetone concentrated extract. The result showed similar improving effect of alcoholism symptoms.

Example 139

Acetone concentrated extract (1.4 g) was obtained by treating as generally described in Example 41 with the exception that the callus of *Centella asiatica* was employed as a plant tissue. The dried calluses were 10 g.

The test was conducted as described in Example 129 using the obtained acetone concentrated extract. The result showed similar improving effect of alcoholism symptoms.

Example 140

Acetone concentrated extract (1.0 g) was obtained by treating as generally described in Example 130 with the exception that whole plant of *C. asiatica* was employed as a plant tissue. The dried calluses were 5.5 g.

The test was conducted as described in Example 129 using the obtained acetone concentrated extract. The result showed similar improving effect of alcoholism symptoms.

What is claimed is:

1. A method for the preparation of 1-sesamine which comprises culturing tissues or cells of a plant belonging to *Hydrocotyle genus* or *Centella genus* in or on a culture medium and extracting the 1-sesamine from the culture cells.

2. A method according to claim 1 wherein the extraction is conducted with an acetone, methanol or ethanol.

* * * * *